United States Patent
Iftikhar et al.

(10) Patent No.: US 10,631,774 B2
(45) Date of Patent: Apr. 28, 2020

(54) MODELLING SYSTEM

(71) Applicant: Conopco, Inc., Englewood Cliffs, NJ (US)

(72) Inventors: Abid Iftikhar, Liverpool (GB); Robert McKeown, Flintshire (GB)

(73) Assignee: Conopco, Inc., Englewood Cliffs, NJ (US)

( * ) Notice: Subject to any disclaimer, the term of this patent is extended or adjusted under 35 U.S.C. 154(b) by 72 days.

(21) Appl. No.: 16/080,834

(22) PCT Filed: Mar. 2, 2017

(86) PCT No.: PCT/EP2017/054969
§ 371 (c)(1),
(2) Date: Aug. 29, 2018

(87) PCT Pub. No.: WO2017/153262
PCT Pub. Date: Sep. 14, 2017

(65) Prior Publication Data
US 2019/0053752 A1    Feb. 21, 2019

(30) Foreign Application Priority Data

Mar. 9, 2016  (EP) .................................. 16159406

(51) Int. Cl.
*A61B 5/00*     (2006.01)
*G01N 33/68*   (2006.01)
*A45D 44/00*   (2006.01)

(52) U.S. Cl.
CPC ............. *A61B 5/448* (2013.01); *G01N 33/68* (2013.01); *A45D 44/005* (2013.01); *A61B 5/441* (2013.01);

(Continued)

(58) Field of Classification Search
None
See application file for complete search history.

(56) References Cited

U.S. PATENT DOCUMENTS

2019/0059559 A1*  2/2019  Iftikhar ................ A61B 5/1077

FOREIGN PATENT DOCUMENTS

WO    WO2014041186    3/2014

OTHER PUBLICATIONS

Ribeiro et al Potential of humancrystallin for hair famage repair; insights into the mechanical properties and bicompatibility international journal of cosmetic science 2013,35, 458-466 (Year 2013).*

(Continued)

*Primary Examiner* — Nancy Bitar
(74) *Attorney, Agent, or Firm* — Foley & Lardner LLP

(57) ABSTRACT

A method of analysing at least one hair surface using a 3D printer includes collecting a first imaging data for the at least one hair surface; applying at least one treatment to the at least one hair surface, the at least one treatment including at least one benefit agent; collecting a second imaging data for the at least one hair surface after applying the at least one treatment; converting the first imaging data into a first formatted data, the first formatted data associated with the 3D printer; converting the second imaging data into a second formatted data, the second formatted data associated with the 3D printer; producing a first 3D model of the at least one hair surface from the 3D printer using the first formatted data; and producing a second 3D model of the at least one hair surface from the 3D printer using the second formatted data.

7 Claims, 1 Drawing Sheet

Untreated fibre

(52) U.S. Cl.
CPC . *G01N 2333/4742* (2013.01); *G01N 2500/00* (2013.01)

(56) References Cited

OTHER PUBLICATIONS

Lee et al "Accuracy of three dimensional printing for manufacturing replica of teeth" the korean journal 217-225 2015 (Year 2015).*
Ou et al ( Cillia et al "3D printed micro pillar structure for surface texture actuation and sensing" CHI 16, Year 2016.*
Search Report and Written Opinion in PCTEP2017054969; dated Mar. 24, 2017.
Monteiro et al.; Morphological Analysis of Polymers on Hair Fibers by SEM and AFM; Materials Research; Dec. 1, 2003; pp. 501-506; XP055270758; vol. 6 No. 4.
Gierad Laput et al.; 3D Printed Hair: Fused Deposition Modeling of Soft strands, Fiberts and Bristles; User Interface Software and Technology; Jan. 1, 2015; pp. 593-597; XP055270761.
Hyung Jin Ahn et al.; An ultrastuctural study of hair fiber damage and restoration following treatment with permanent hair dye; International Journal of Dermatology; Feb. 1, 2002; pp. 88-92; XP055270760; vol. 41 No. 2.
Gould et al.; Electron-microscopy-image analysis: Quantification of ultrastructural changes in hair fiber cross sections as a result of cosmetic treatment presented at the Society of Cosmetic Chemists Annual Meeting; Journal of the Society of Cosmetic Chemists; Jan. 1, 1985; pp. 53-59; XP055270759; vol. 36.
Search Report and Written Opinion in EP16159406; dated May 12, 2016.
Search Report and Written Opinion in EP16159407; dated May 12, 2016; European Patent Office (EPO).
Search Report and Written Opinion in PCTEP2017054962; dated Mar. 27, 2017.
Designing New Materials and Manufacturing Techniques 2016; Cillia_3D_Printed_MicroPillar_Structures; 12 pages, Year 2016 ; Cheng et al.
The Korean Journal of Orthodontics; Accuracy of three-dimensional printing for manufacturing replica teeth; 9 pages, Mar. 26, 2015, Lee et al.
International Journal of Cosmetic Science; Potential of human D-crystallin for hair damage repair; 10 pages, Ribeiro et al Year 2013.

* cited by examiner

Untreated fibre

Showing PSA deposition on hair from a 2% shampoo

Showing PSA silicone deposition on hair from a conditioner

MODELLING SYSTEM

CROSS-REFERENCE TO RELATED APPLICATIONS

This application claims priority to International Patent Application No. PCT/EP2017/054969, filed on Mar. 2, 2017, and European Patent Application No. 16159406.4, filed on Mar. 9, 2016, both of which are incorporated herein by reference in their entireties.

FIELD OF THE INVENTION

The present invention relates to a method of analysing the effect of benefit agents on hair, delivered from hair treatment compositions, the deposition behaviour thereof, and of recommending a suitable hair treatment.

BACKGROUND

VALERIA FERNANDES MONTEIRO ET AL: "Morphological analysis of polymers on hair fibers by SEM and AFM", MATERIALS RESEARCH, vol. 6, no. 4, 1 Dec. 2003, pages 501-506, XP055270758, BR; and JACALYN G GOULD ET AL: "Electron microscopy-image analysis: Quantification of ultrastructural changes in hair fiber cross sections as a result of cosmetic treatment; Presented at the Society of Cosmetic Chemists Annual Meeting", J. SOC. COSMET. CHEM, vol. 36, 1 Jan. 1985, pages 53-59, XP055270759 disclose imaging and microscope-based approaches for analysing the effect of treatments on hair fibres.

HYUNG JIN AHN ET AL: "An ultrastuctural study of hair fiber damage and restoration following treatment with permanent hair dye", INTERNATIONAL JOURNAL OF DERMATOLOGY, vol. 41, no. 2, 1 Feb. 2002, pages 88-92, XP055270760, UK; discloses an ultra-structural study of hair fibre damage and restoration using electron microscopy.

GIERAD LAPUT ET AL: "3D Printed Hair: Fused Deposition Modelling of Soft Strands, Fibers and Bristles", USER INTERFACE SOFTWARE AND TECHNOLOGY, 1 Jan. 2015, pages 593-597, XP055270761, discloses the production of hair fibres by 3D printing.

WO14041186A1 describes a system or component such as software for 3D modelling of bodies.

Assaults such as treatments, protocols and hair care regimes are known to cause damage to the surface and structure of hair. Remedial and beneficial treatments are available to mitigate these detrimental effects but the concept can be difficult for the consumer to grasp and the full effects of the remedial treatments difficult to fully comprehend.

The method of the invention can be used to assess properties of hair fibres, which have been exposed to various remedial and beneficial treatments. In this way it is possible to demonstrate any surface improvement, such as "smoothing", arising from the application of the treatment to the hair. It also becomes possible to recommend a suitable product according to an individual's need.

SUMMARY

In a first aspect, the present invention provides a method of analysing the effect and deposition of remedial and beneficial treatments on hair, comprising the steps of:

(i) collecting imaging data for at least one hair surface, (ii) applying at least one treatment, comprising at least one benefit agent, to the hair surface, to deposit the benefit agent onto the hair surface, (iii) collecting imaging data for the hair surface arising from step (ii), (iv) converting the imaging data collected at steps (i) and (iii) into a format to create magnified images from a 3D printer, (v) producing magnified 3D models of the hair surface from a 3D printer using the data from step iv, (vi) comparing the 3D model arising from step (iii) to the 3D model arising from step (i), (vii) analyzing the deposition behavior of the benefit agent, (viii) analyzing any consumer perceivable effect resulting from step (ii), and (ix) correlating the analysis of step (vii) to the analysis of step (viii).

Preferably, steps (ii) to (vi) are repeated. Steps (ii) to (vi) may be repeated multiple times in order to enable assessment of the impact of repeated or long term exposure to the benefit agent. For example, from 2 to 20 times, preferably from 2 to 8 times.

This method allows the properties shown in the magnified image/3D model at step (v) of the method of the invention to be compared to the initial image/3D model from step (i).

Properties that may be seen in the magnified image obtained at the initial stage (i) are external topographical aspects of the hair fibre, for example, cuticle lift, cuticle damage (for example, chipping, splitting, change in shape and breaking), cuticle erosion, split ends, kinks, blobs, cracks, holes and knots. The extent to which these are present at the initial imaging stage (i) depends on the age and condition of the hair at the beginning of the method.

Different benefit agents are deposited onto hair surfaces in different ways and the nature of the deposition can affect the benefit perceived by the consumer. For example, deposition may occur in layers or as discrete particles, and at different locations on the hair surface. These aspects are conferred at step (ii) of the method, and are apparent from step (v).

Examples of benefit agents that may be deposited onto hair surfaces include hair conditioning agents such as silicones, lipids and oils; styling polymers; waxes, sunscreens, bodyfying agents and mixtures thereof.

A preferred silicone is DC5-7134 (ex Dow Corning). A preferred styling polymer is PSA Acudyne MD5800 (ex Dow Corning).

Consumer perceivable effects are any changes, perceived by the consumer, as a result of the treatment with the benefit agent, including for example, changes to the perception of damage, the perception of protection or the perception of repairing. These can be perceived by properties such as rough feel, smoothness, softness, harshness, dryness, moisturisation, ease of combing and friction.

It is possible to recommend a suitable product according to an individual's need, that targets the properties of the hair.

The method of the invention may be used in an educational tool, in communication with press, media or trade, at point of sale, in professional environments such as salons, and in commercial material, advertisement material and promotional material.

BRIEF DESCRIPTION OF THE DRAWINGS

The details of one or more implementations are set forth in the accompanying drawings and the description below. Other features, aspects, and advantages of the disclosure will become apparent from the description, the drawings, and the claims, in which:

DETAILED DESCRIPTION

The Image

Figure 1:
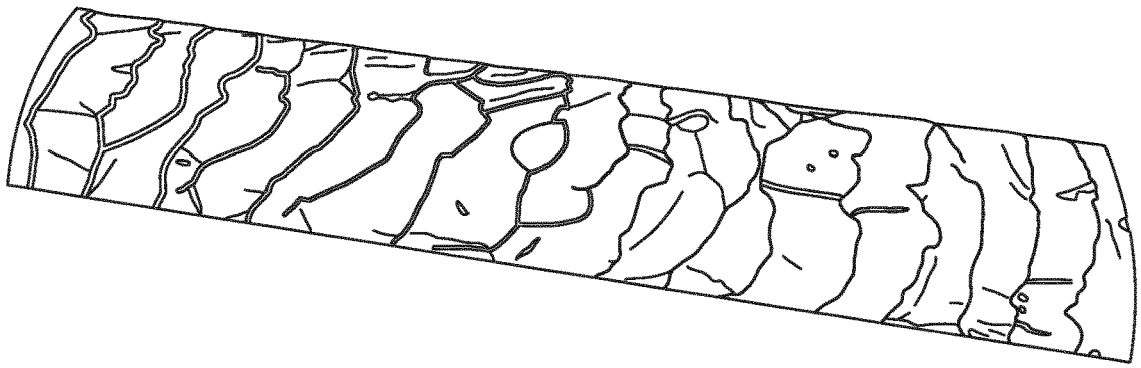
FIG. 1 is a 3D printable image of an untreated hair fibre.

Preferably, the image is a topographic surface image; more preferably, the topographic surface image is produced using a 3D optical profiler, such as a Sensofar S neox, or laser profilometer.

The topographic surface is converted into a format suitable for a 3D printer, preferably it is exported in a digital file as spatial coordinates (X, Y, Z) of each point which describes the topographic (3D) surface. Preferably, this is completed using a profilometer. An example of a suitable profilometer is the Sensofar S neox profilometer that can produce a 3d image of the surface to be studied. The profilometer software, for example sensoSCAN v5, can export a file ".dat" that is a list of all the X, Y, Z coordinates of each point.

Preferably, the magnified 3D image has a magnification of from 100 to 50,000, preferably 30,000 times.

If desired the conversion of the imaging data iv) comprises a magnification process. The magnification is preferably achieved by change of resolution, units and/or rescale of coordinate axis, producing a new digital file with the new spatial coordinates. A preferred way of magnifying the data points is using Matlab. In this preferred method the ".dat" file is imported in Matlab as a matrix and a set of Matlab scripts are used to manipulate the matrix and change the resolution/scale. It is highly preferred if the matrix is exported into a new ASCII file ".XYZ" as a list of all the X, Y, Z coordinates of each point.

The imaging data is converted into an image suitable for a 3D printer. Preferably, the file is imported in a 3D-CAD software and the 3D surface is applied onto a face of a parallelogram to obtain a 3D object. The resulting 3D image is exported to a digital file compatible with the 3D-printer device software. The XYZ file is preferably imported into a software conversion package, for example the "Rhino" software package, which can convert it into a 3d file and export as a .STL file.

The 3D image is printed to form a 3D object. This can be achieved by using any of the modern 3D printers available, an example is EOS (Electro Optical Systems) EOSINT P380 Selective Laser Sintering printer and a 3D replica of the magnified surface produced.

Preferably, a colour rinse is applied to the 3D model to highlight the areas of interest. The colours can be varied according to the surface height. This is useful in showing up extent of cuticle lift and depth of holes, etc.

The Hair

The method of the invention can be carried out on a single hair fibre, or a bundle of hair fibres.

The hair is preferably human hair.

Beneficial and Remedial Treatments

A preferred type of treatments are those that reduce or alleviate the effects of damage to the hair. A further preferred type of treatment are styling treatments.

Preferred treatments for hair are rinse off and leave on products. Leave on products include conditioning products and styling products such as mousses, waxes, creams and gels.

Preferred hair treatment compositions are selected from a shampoo, a rinse-off hair conditioner, a hair mask, a leave-on conditioner composition, and a pre-treatment composition, more preferably selected from a rinse-off hair conditioner, a hair mask, a leave-on conditioner composition, and a pre-treatment composition and most preferably selected from a rinse-off hair conditioner, a hair mask and a leave-on conditioner composition. An example of a suitable pre-treatment composition is an oil treatment.

Rinse off conditioners for use in the invention are conditioners that are typically left on wet hair for 1 to 2 minutes before being rinsed off.

Hair masks for use in the present invention are treatments that are typically left on the hair for 3 to 10 minutes, preferably from 3 to 5 minutes, more preferably 4 to 5 minutes, before being rinsed off.

Leave-on conditioners for use in the invention are typically applied to the hair and left on the hair for more than 10 minutes, and preferably are applied to the hair after washing and not rinsed out until the next wash.

Treatments compositions for use in the method of the current invention preferably comprise conditioning agents. Conditioning agents are preferably selected from cationic surfactants, used singly or in admixture.

Cationic surfactants useful in compositions for use in the method of the invention contain amino or quaternary ammonium hydrophilic moieties which are positively charged when dissolved in aqueous composition.

Examples of suitable cationic surfactants are those corresponding to the formula $$[N(R_1)(R_2)(R_3)(R_4)]^+(X)^-$$

in which $R_1$, $R_2$, $R_3$ and $R_4$ are independently selected from (a) an aliphatic group of from 1 to 22 carbon atoms, or (b) an aromatic, alkoxy, polyoxyalkylene, alkylamido, hydroxyalkyl, aryl or alklaryl group having up to 22 carbon atoms; and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

The most preferred cationic surfactants for compositions for use in the method of the present invention are monoalkyl quarternary ammonium compounds in which the alkyl chain lengthy is $C_8$ to $C_{14}$.

Suitable examples of such materials correspond to the formula

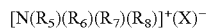

in which $R_5$ is a hydrocarbon chain having 8 to 14 carbon atoms or a functionalised hydrocarbyl chain with 8 to 14 carbon atoms and containing ether, ester, amido or amino moieties present as substituents or as linkages in the radical chain, and $R_6$, $R_7$ and $R_8$ are independently selected from (a) hydrocarbyl chains of from 1 to about 4 carbon atoms, or (b) functionalised hydrocarbyl chains having from 1 to about 4 carbon atoms and containing one or more aromatic, ether, ester, amido or amino moieties present as substituents or as linkages in the radical chain, and X is a salt-forming anion such as those selected from halogen, (e.g. chloride, bromide), acetate, citrate, lactate, glycolate, phosphate nitrate, sulphate and alkylsulphate radicals.

The functionalised hydrocarbyl chains (b) may suitably contain one or more hydrophilic moieties selected from alkoxy (preferably 01-03 alkoxy), polyoxyalkylene, alkylester, and combinations thereof.

Preferably the hydrocarbon chains $R_1$ have 12 to 14 carbon atoms, most preferably 12 carbon atoms. They may be derived from source oils which contain substantial amounts of fatty acids having the desired hydrocarbyl chain length. For example, the fatty acids from palm kernel oil or coconut oil can be used as a source of $C_8$ to $C_{12}$ hydrocarbyl chains.

Typical monoalkyl quarternary ammonium compounds of the above general formula for use in compositions for use in the method of the invention include:

(i) Lauryl trimethylammonium chloride (available commercially as Arquad C35 ex Akzo); cocodimethyl benzyl ammonium chloride (available commercially as Arquad DMCB-80 ex-Akzo)

(ii) Compounds of the formula:

wherein:

x+y is an integer from 2 to 20;

$R_1$ is a hydrocarbyl chain having 8 to 14, preferably 12 to 14, most preferably 12 carbon atoms and containing ether, ester, amido or amino moieties present as substituent's or as linkages in the radical chain;

$R_2$ is a 01-03 alkyl group or benzyl group, preferably methyl, and

X is a salt-forming anion such as those selected from halogen, (e.g. chloride, bromide), acetate, citrate, lactate, glycolate, phosphate nitrate, sulphate, methosulphate and alkylsulphate radicals.

Suitable examples are PEG-n lauryl ammonium chlorides (where n is the PEG chain length), such as PEG-2 cocomonium chloride (available commercially as Ethoquad C12 ex-Akzo Nobel); PEG-2 cocobenzyl ammonium chloride (available commercially as Ethoquad CB12 ex-Akzo Nobel); PEG-5 cocomonium methosulphate (available commercially as Rewoquat CPEM ex Rewo); PEG-15 cocomonium chloride (available commercially as Ethoquad C/25 ex-Akzo).

(iii) Compounds of the Formula:

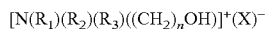

wherein:

n is an integer from 1 to 4, preferably 2;

$R_1$ is a hydrocarbyl chain having 8 to 14, preferably 12 to 14, most preferably 12 carbon atoms;

$R_2$ and $R_3$ are independently selected from $C_1$-$C_3$ alkyl groups, and are preferably methyl, and X– is a salt-forming anion such as those selected from halogen, (e.g. chloride, bromide), acetate, citrate, lactate, glycolate, phosphate nitrate, sulphate, alkylsulphate radicals. Suitable examples are lauryldimethylhydroxyethylammonium chloride (available commercially as Prapagen HY ex-Clariant).

Mixtures of any of the foregoing cationic surfactants compounds may also be suitable.

Examples of suitable cationic surfactants for use in hair compositions for use in the method of the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant is cetyltrimethylammonium chloride, available commercially, for example as DEHYQUART, ex Henkel.

The level of cationic surfactant is preferably from 0.01 to 10, more preferably 0.05 to 5, most preferably 0.1 to 2 w.t. % of the total composition.

A preferred conditioner comprises a conditioning gel phase. Such conditioners and methods for making them are described in WO2014/016354, WO2014/016353, WO2012/016352 and WO2014/016351.

The conditioning compositions may also comprise other optional ingredients. Such ingredients include, but are not limited to; fatty material, deposition polymers and further conditioning agents.

Conditioner compositions preferably additionally comprise fatty materials. The combined use of fatty materials and cationic surfactants in conditioning compositions is believed to be especially advantageous, because this leads to the formation of a structured lamellar or liquid crystal phase, in which the cationic surfactant is dispersed.

By "fatty material" is meant a fatty alcohol, an alkoxylated fatty alcohol, a fatty acid or a mixture thereof. Preferably, the alkyl chain of the fatty material is fully saturated.

Representative fatty materials comprise from 8 to 22 carbon atoms, more preferably 16 to 22. Examples of suitable fatty alcohols include cetyl alcohol, stearyl alcohol and mixtures thereof. The use of these materials is also advantageous in that they contribute to the overall conditioning properties of compositions.

Alkoxylated, (e.g. ethoxylated or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof. The level of fatty material in conditioners is suitably from 0.01 to 15, preferably from 0.1 to 10, and more preferably from 0.1 to 5 percent by weight of the total composition. The weight ratio of cationic surfactant to fatty alcohol is suitably from 10:1 to 1:10, preferably from 4:1 to 1:8, optimally from 1:1 to 1:7, for example 1:3.

Further conditioning ingredients include esters of fatty alcohol and fatty acids, such as cetyl palmitate.

A conditioning composition for use in the present invention may preferably comprise a miscellar structured liquid.

The pH of a conditioner comprising the present composition is preferably 3-5. More preferably the pH of the composition is 4.5-5.5.

Where the composition has a pH of less than 3.10 it is preferred that it is in the form of a conditioning mask for intense treatment.

Further conditioning ingredients include conditioning oils, preferably selected from coconut oil and olive oil.

The invention will now be illustrated by the following non-limiting Examples:

EXAMPLES

Specimen hair fibres were sampled from a human head and an untreated specimen was imaged according to the method below. The fibres were then treated with silicone or a styling polymer, and imaged as before.

The silicone was DC5-7134 (ex Dow Corning).

The styling polymer was a pressure sensitive adhesive (PSA) available as Acudyne MD5800 (ex Dow Corning).

The silicone was incorporated into a conditioner base, whilst the PSA was prepared in a shampoo base.

The shampoo composition, comprising PSA styling polymer is shown in Table 2.

TABLE 2

Composition of shampoo comprising PSA

| Material | Weight % in composition |
|---|---|
| Acudyne MD 5800[1] (55% active) | 3.64% |
| Carbopol ® 980[2] (4% active) | 10% |
| Sodium hydroxide (50% active) | 0.43% |
| Sodium Laureth Sulphate (70% active) | 17.14% |
| Cocoamidopropyl betaine[3] (30% active) | 5.33% |
| Jaguar C14 S[4] | 0.2% |
| Water and minors | To 100% |

[1]Acudyne MD5800 is an acrylic PSA available from Dow Corning
[2]Carbopol ® 980 is a crosslinked polyacrylate polymer available from Lubrizol
[3]supplied by Galaxy
[4]Jaguar C14 S is Guar Hydroxypropyl Trimonium Chloride polymer available from Rhodia The shampoo composition was prepared using the following method;

Heating the water to 30° C. and stirring using an overhead stirrer and paddle (e.g. Heidolph). Adding the PSA emulsion and stirring until thoroughly mixed. Adding each of the remaining ingredients individually and allowing the composition to thoroughly mix between each addition. Adjusting the pH and viscosity as required using NaCl and NaOH.

Hair was treated with the shampoo using the following method:—

The hair fibres were held under running water for 30 seconds, shampoo applied using a non-hypodermic syringe in a dose of 0.1 ml of shampoo per 1 g of hair and rubbed into the hair for 30 seconds. Excess lather was removed by holding under running water for 30 seconds and the shampoo stage repeated. The hair was rinsed under running water for 1 minute and excess water removed using a wipe.

The conditioner composition, comprising silicone is shown in Table 3 and may be prepared by the following method;

Heating the water to 81° C. and stirring using an overhead stirrer and paddle (e.g. Heidolph). Mixing in the fatty materials and the surfactant. Maintaining heat and stirring for 30 minutes. Cooling the mixture and mixing in the remaining ingredients. Mixing at high shear for 5 minutes (e.g. using a Silverson mixer).

TABLE 3

Composition of conditioner comprising DC5-7134

| Material | Weight % in composition |
|---|---|
| Lactic acid (85% active) | 0.38% |
| Stearamidopropyl Dimethylamine | 1.25% |
| Cetearyl Alcohol | 5.00% |
| Behentrimonium Chloride & Dipropylene Glycol[2] (68.5% active) | 1.25% |
| Sodium chloride | 0.10% |
| Silicone DC 5-7134[3] (70% active) | 1.45% |
| Water and minors | To 100% |

1 - DC5-7134 available from Dow Corning
[2]trade name Genamin BTLF supplied by Aako
[3]Silicone DC 5-71334 supplied by Dow Corning Hair was treated with the conditioner using the following method:—

The hair fibres were held under running water for 30 seconds. Conditioner was then applied to the hair by a non-hypodermic syringe in a dose of 0.2 ml of conditioner per 1 g of hair and massaged into the hair for 1 minute. The hair was rinsed under running water for 1 minute and excess water removed using a wipe.

Imaging Method

The topographic surface of the hair fibres was converted into a format suitable for a 3D printer, by exporting in a digital file as spatial coordinates (X, Y, Z) of each point which describes the topographic (3D) surface using a sensoSCAN v5 with a Sensofar S neox profilometer.

The resulting digital file data was magnified by importing to Matlab as a matrix and using Matlab scripts to manipulate the matrix and change the resolution/scale. The matrix was then exported into a new ASCII file ".XYZ" as a list of all the X, Y, Z coordinates of each point. The magnification was 30,000 times.

The imaging data was converted into an image suitable for a 3D printer using 3D-CAD software and the 3D surface was applied onto a face of a parallelogram to obtain a 3D object. The resulting 3D image was exported to a digital file compatible with the 3D-printer device software by use of the "Rhino" software package, which converted it into a 3D file and exported it as a .STL file.

The 3D image was then printed to form a 3D object. This was achieved by using an EOS (Electro Optical Systems) EOSINT P380 Selective Laser Sintering printer and a 3D replica of the magnified surface produced.

Comparing the resulting 3D images demonstrated the effect of the treatments on the hair.

Figure 2:
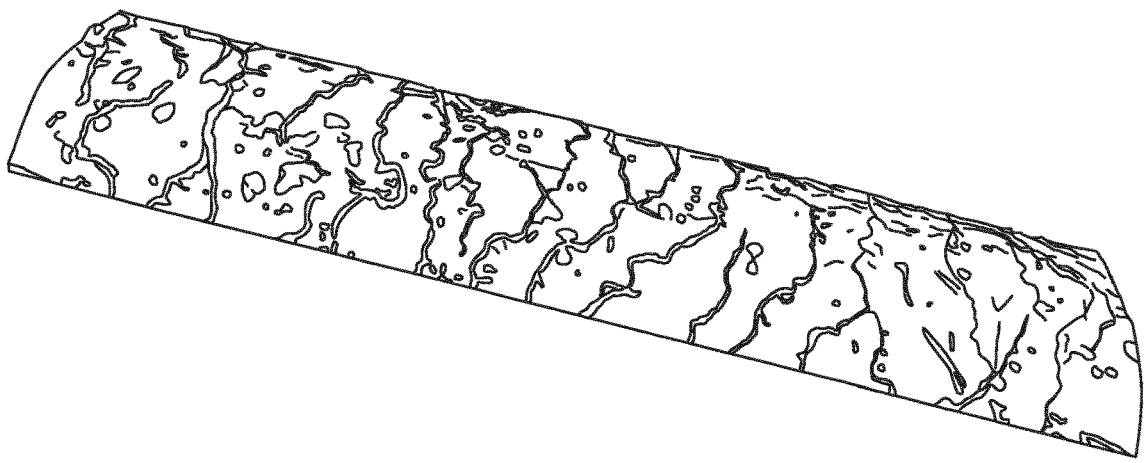
FIG. 2 is a 3D printable image of a hair fibre that has been treated.
Figure 3:
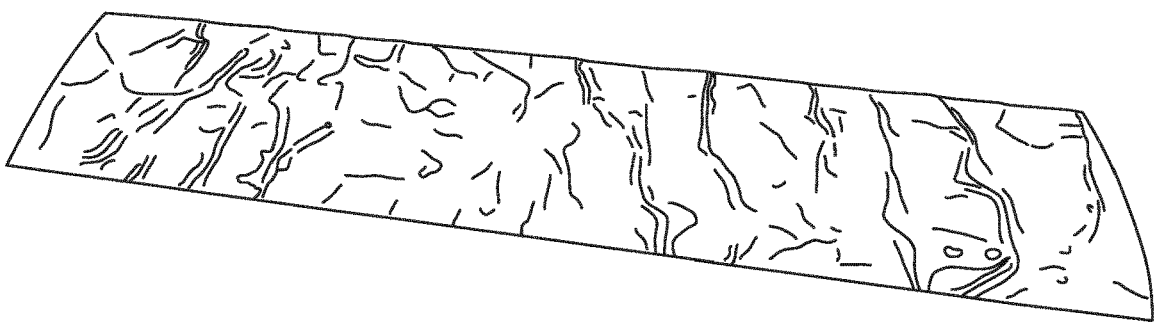
FIG. 3 is a 3D printable image of another hair fibre that has been treated.

The results are shown in FIGS. 1, 2 and 3, where:—

FIG. 1 is a 3D printable image of an untreated hair fibre.

FIG. 2 is a 3D printable image of hair that has been treated with shampoo comprising PSA styling polymer.

FIG. 3 is a 3D printable image of a hair fibre that has been treated with conditioner comprising silicone.

It can be seen that the treatments clearly had an impact on the surface of the hair. Silicone was deposited as a layer along the length of the fibre, thus having a beneficial smoothing effect to raised or chipped cuticles. Particles of styling polymer (i.e. pressure sensitive adhesive) were deposited in discrete blobs on the cuticles. This caused increased friction and conferred a styling benefit and shape benefit and longevity of hold. Thus it is possible to recommend highly suitable treatments to suit individual hair needs.

The invention claimed is:

1. A method of analysing at least one hair surface using a 3D printer, the method comprising:
    collecting a first imaging data for the at least one hair surface,
    applying at least one treatment to the at least one hair surface, the at least one treatment comprising at least one benefit agent,
    collecting a second imaging data for the at least one hair surface after applying the at least one treatment,
    converting the first imaging data into a first formatted data, the first formatted data associated with the 3D printer,
    converting the second imaging data into a second formatted data, the second formatted data associated with the 3D printer,
    producing a first 3D model of the at least one hair surface from the 3D printer using the first formatted data,
    producing a second 3D model of the at least one hair surface from the 3D printer using the second formatted data,
    comparing the second 3D model to the first 3D model,
    performing an analysis of a deposition behavior of the at least one benefit agent,
    performing an analysis of analyzing any consumer perceivable effect associated with the at least one treatment, and
    correlating the analysis of the deposition behavior to the analysis of the any consumer perceivable effect.

2. The method of claim 1, further comprising, after correlating the analysis of the deposition behavior to the analysis of the any consumer perceivable effect:
    applying at least one treatment to the at least one hair surface,
    collecting a third imaging data for the at least one hair surface,
    converting the third imaging data into a third formatted data, the third formatted data associated with the 3D printer,
    producing a third 3D model of the at least one hair surface from the 3D printer using the third formatted data, and
    comparing the third 3D model to the first 3D model.

3. The method of claim 1, wherein the at least one benefit agent is at least one of a shampoo, a rinse-off hair conditioner, a hair mask, a leave-on treatment composition, or a pre-treatment composition.

4. The method of claim 1, wherein the at least one benefit agent is at least one of a silicone, a lipid, an oil, a styling polymer, a wax, a sunscreen, a bodyfying agent, or a mixture.

5. The method of claim 1, wherein applying the at least one treatment to the at least one hair surface comprises depositing the at least one treatment onto the at least one hair surface in layers or as discrete particles.

6. The method of claim 1, further comprising before comparing the second 3D model to the first 3D model:
    determining a first area of interest on the first 3D model;
    applying a first colour rinse to the first area of interest
    determining a second area of interest on the second 3D model; and
    applying a second colour rinse to the second area of interest.

7. The method of claim 1, wherein converting the first imaging data into the first formatted data comprises magnifying the first imaging data 30,000 times, and
    wherein converting the second imaging data into the second formatted data comprises magnifying the second imaging data 30,000 times.

* * * * *